(12) United States Patent
Jiang

(10) Patent No.: US 10,675,375 B2
(45) Date of Patent: Jun. 9, 2020

(54) MULTIFUNCTIONAL MICROWAVE PLASMA AND ULTRAVIOLET LIGHT DEODORIZATION TREATMENT DEVICE

(71) Applicant: Chengdu Tiantian Medical Electric Apparatus Science And Technology Co., Ltd., Chengdu, Sichuan Province (CN)

(72) Inventor: Tianhua Jiang, Chengdu (CN)

( * ) Notice: Subject to any disclaimer, the term of this patent is extended or adjusted under 35 U.S.C. 154(b) by 0 days.

(21) Appl. No.: 16/246,404

(22) Filed: Jan. 11, 2019

(65) Prior Publication Data
US 2019/0209729 A1    Jul. 11, 2019

(30) Foreign Application Priority Data
Jan. 11, 2018  (CN) .......................... 2018 1 0026456

(51) Int. Cl.
| | | |
|---|---|---|
| *A61L 9/22* | (2006.01) | |
| *H01J 37/32* | (2006.01) | |
| *A61L 9/014* | (2006.01) | |
| *A61L 9/04* | (2006.01) | |
| *A61L 9/20* | (2006.01) | |
| *B01D 53/00* | (2006.01) | |
| *B01D 53/04* | (2006.01) | |

(Continued)

(52) U.S. Cl.
CPC .................. *A61L 9/22* (2013.01); *A61L 9/014* (2013.01); *A61L 9/046* (2013.01); *A61L 9/20* (2013.01); *B01D 53/007* (2013.01); *B01D 53/04* (2013.01); *B01D 53/32* (2013.01); *B01D 53/38* (2013.01); *B01D 53/75* (2013.01); *B01D 53/76* (2013.01); *B01D 53/8678* (2013.01); *H01J 37/32174* (2013.01); *H01J 37/32311* (2013.01); *A61L 2209/11* (2013.01); *A61L 2209/12* (2013.01); *A61L 2209/14* (2013.01); *A61L 2209/15* (2013.01); *A61L 2209/212* (2013.01); *A61L 2209/22* (2013.01); *B01D 2253/102* (2013.01); *B01D 2255/2027* (2013.01); *B01D 2255/70* (2013.01); *B01D 2257/90* (2013.01); *B01D 2258/06* (2013.01); *B01D 2259/804* (2013.01); *B01D 2259/818* (2013.01)

(58) Field of Classification Search
CPC ..... A61L 9/14; A61L 9/16; A61L 9/18; A61L 9/22; A61L 9/046
USPC ........................................................ 250/435
See application file for complete search history.

(56) References Cited

U.S. PATENT DOCUMENTS 6,150,663 A * 11/2000 Rosenthal ................. A23L 2/50
250/435

* cited by examiner

*Primary Examiner* — Jason L McCormack
(74) *Attorney, Agent, or Firm* — Novoclaims Patent Services LLC; Mei Lin Wong

(57) ABSTRACT

A multifunctional microwave plasma and ultraviolet light deodorization treatment unit, which includes: a rapid decomposition device (1), a high frequency plasma electric field (2), a microwave plasma electric field (3), a high intensity ultraviolet radiation field (4), a low temperature plasma electric field (5), a high intensity ozone gas reaction chamber (6), a reaction termination chamber (7) and a clean gas organization chamber (8) sequentially installed inside a horizontal rectangular box which has an elongated body defining a horizontal axis and has a channel cavity therein. The deodorization treatment unit further includes an exhaust gas odor collecting pipe and an odor gas storage cabinet (9) connected to an air pump (10), the air pump (10) is connected to an odor gas inlet of the rapid decomposition device (1), the clean gas organization chamber (8) has one end connected to a clean gas exhaust pipe.

7 Claims, 11 Drawing Sheets

(51) Int. Cl.
*B01D 53/32* (2006.01)
*B01D 53/75* (2006.01)
*B01D 53/76* (2006.01)
*B01D 53/86* (2006.01)
*B01D 53/38* (2006.01)

MULTIFUNCTIONAL MICROWAVE PLASMA AND ULTRAVIOLET LIGHT DEODORIZATION TREATMENT DEVICE

CROSS REFERENCE OF RELATED APPLICATION

This application claimed priority of the application number 201810026456.3, filing date Jan. 11, 2018 filed in China. The contents of these specifications, including any intervening amendments thereto, are incorporated herein by reference.

BACKGROUND OF THE PRESENT INVENTION

Field of Invention

The present invention relates to equipment for deodorization treatment for odorous exhaust gas from pharmaceutical plant.

Description of Related Arts

The odor collection and treatment of sewage treatment plants are widely used in foreign countries. In China, not many sewage treatment plants process large-scale odor collection and treatment. The sewage plants with large-scale imported deodorization device mainly include Macao Hazel Wastewater Treatment Plant and Nanjing Chengbei Wastewater Treatment Plant which utilize biological or chemical methods for deodorization. Small sewage treatment plants utilize deodorization method with adsorbents, which is mainly because foreign deodorization equipment is expensive, both of its initial installation and operation cost, and repair and maintenance cost are high. The domestic exhaust gas deodorization technology starts late, and there are not many mature products.

The existing deodorization control technology includes: 1. Spraying deodorant and flushing agent to cover and oxidize the odorous compounds. 2. Chemicals are directly applied into the sewage to prevent the formation of nitrogen or sulfur chain reactants. 3. Odor collection and UV treatment. Now, the most widely used is the third one, which is odor collection and UV treatment.

SUMMARY OF THE PRESENT INVENTION

An object of the present invention is to provide a multifunctional microwave plasma and ultraviolet deodorization treatment unit.

Accordingly, the multifunctional microwave plasma and ultraviolet light deodorization treatment unit comprises: a rapid decomposition device (1), a high frequency plasma electric field (2), a microwave plasma electric field (3), a high intensity ultraviolet radiation field (4), a low temperature plasma electric field (5), a high intensity ozone gas reaction chamber (6), a reaction termination chamber (7) and a clean gas organization chamber (8) sequentially installed on a wall of a horizontal rectangular box 100, the horizontal rectangular box 100 has a channel cavity in the middle of the horizontal axis thereof. The exhaust gas odor collecting pipe and the odor gas storage cabinet (9) are connected to an air pump (10). The air pump (10) is connected to an odor gas inlet of the rapid decomposition device (1), and the clean gas exhaust pipe 104 is connected at one end of the clean gas organization chamber (8), wherein:

the rapid decomposition device (1) comprises activated carbon for adsorption function, the rapid decomposition device (1) has a monofluoro atom oxide catalyst, and the monofluoro atom oxide catalyst is commercially available under the trade name sodium monofluorophosphate, and the chemical formula is $Na_2PO_3F$;

the high frequency plasma electric field (2) comprises: a high frequency plasma electric field generator;

the microwave plasma electric field (3) comprises: a control which is connected to a high voltage power supply (39), the high voltage power supply (39) is connected to the magnetron (32), the microwave plasma electric field (3) has a fixed partition panel (33), and a quartz tube (31) is mounted to the fixed partition panel (33). The magnetron (32) is mounted on the casing of the microwave plasma electric field (3); the quartz tube (31) is filled with an inert gas and mercury, and the entire quartz tube is uniformly discharged in the microwave plasma electric field (3), producing a full-band UV at 180~380 nm and ozone, and ultraviolet light and ozone are used for sterilization;

the high intensity ultraviolet radiation field (4) comprises: a controller (45) which is connected in parallel with a plurality of ballasts (44), each ballast (44) is connected to a high intensity ultraviolet generator (42), and all of the high intensity ultraviolet generators (42) are mounted inside a cavity (46) of the high intensity ultraviolet radiation field (4);

the multifunctional microwave plasma and ultraviolet deodorization treatment unit, characterized in that: the low temperature plasma electric field (5) comprises: inside a casing (52) of the low temperature plasma electric field (5), an inlet air filter (54) mounted proximal to an air inlet (51) of the low temperature plasma electric field (5), an outlet air filter (57) mounted proximal to the low temperature plasma electric field (5) the air outlet (56), and a low temperature plasma electric field generator (55) mounted in the middle of the casing (52) of the low temperature plasma electric field (5);

the high intensity ozone gas reaction chamber (6) comprises: an air compressor (61) connected to an air source gas pipe (62), the air source gas pipe (62) connected in parallel to a plurality of ozone generators (63), and a gas outlet of each of the ozone generators (63) are connected to the ozone gas pipe (64), the ozone gas pipe (64) has one end connected to the ozone gas inlet (672) at the bottom side (671) of the high intensity ozone gas reaction cavity (67).

The multifunctional microwave plasma and ultraviolet deodorization treatment unit, characterized in that: the reaction termination chamber (7) comprises: a plurality of honeycomb activated carbon filters (73) installed on the reaction termination chamber body (72), and the honeycomb activated carbon filter (73) is covered with pure carbon (75);

the clean gas organization chamber (8) comprises a clean gas organization chamber body (82), and a plurality of positive and negative ion generators (83) are mounted on a frame of the clean gas organization chamber body (82).

The multifunctional microwave plasma and ultraviolet deodorization treatment unit, characterized in that: the microwave plasma circuit of the microwave plasma electric field (3) comprises: an integrated circuit IC1, which has a model number of MAX038, and an integrated circuit IC2, which has a model number of LF353.

The multifunctional microwave plasma and ultraviolet light deodorization treatment unit, characterized in that: the horizontal rectangular box comprises a plurality of doors at a front end thereof such that the horizontal rectangular box can be open conveniently and easily.

The multifunctional microwave plasma and ultraviolet light deodorization treatment unit of the present invention overcomes the existing problems of large investment, high energy consumption, slow absorption, high running cost and large maintenance workload in the conventional arts. The deodorization treatment unit of the present invention only requires 3 kW for main engine power, and one deodorization treatment unit can reach a maximum purifying capacity of 50~3000 cubic meters per hour; the deodorization treatment unit is quick and convenient to install, and the running cost is only one tenth of the traditional purification equipment. The deodorization treatment unit has the unique features of automatic, high efficiency, energy saving and environmental protection, achieving the most ideal exhaust gas purification effect.

DETAILED DESCRIPTION OF THE PREFERRED EMBODIMENT

Figure 1:
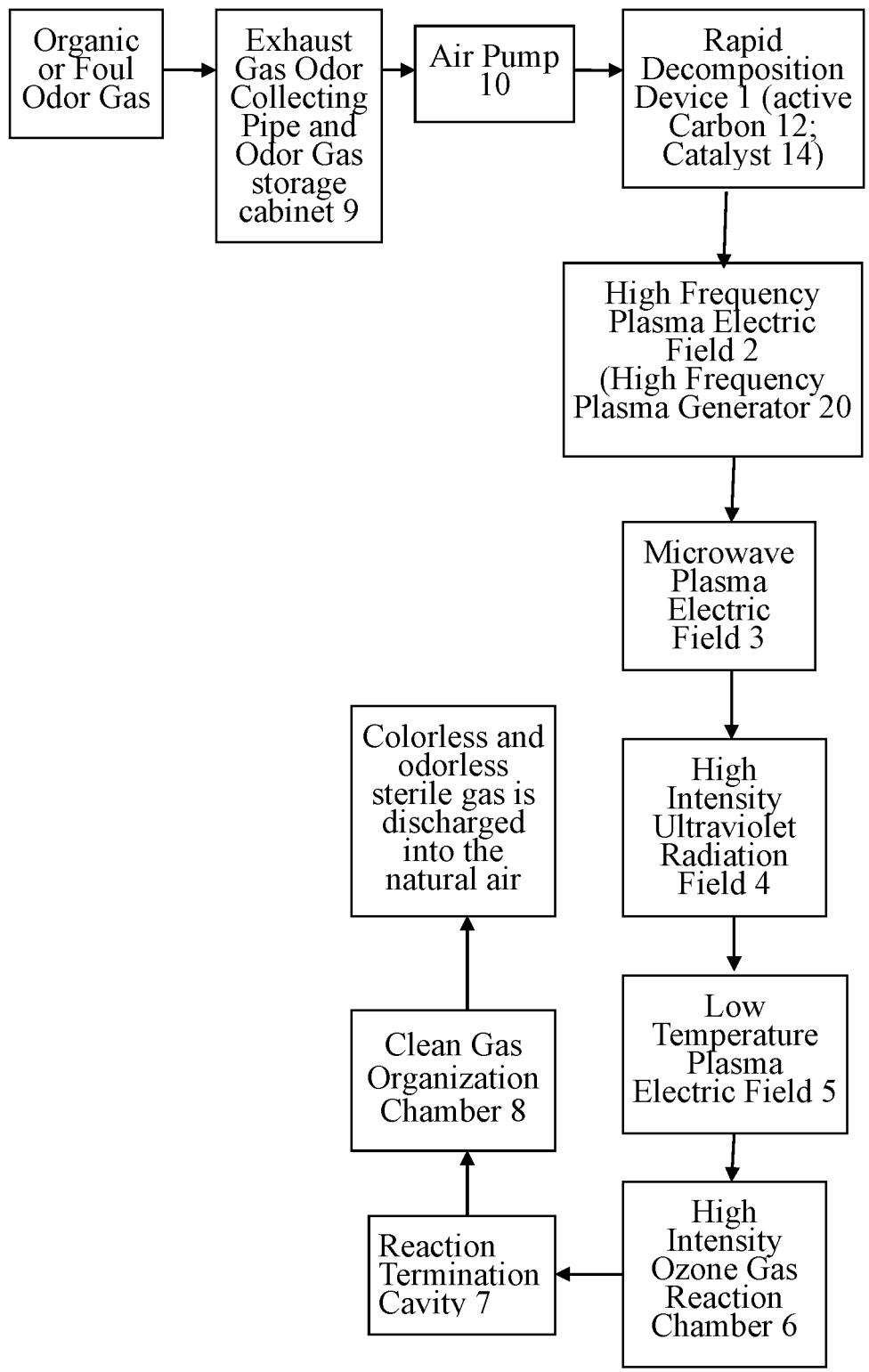
FIG. 1 is a block diagram showing the structure of a multifunctional microwave plasma and ultraviolet deodorization treatment unit according to the preferred embodiment of the present invention.
Figure 6:
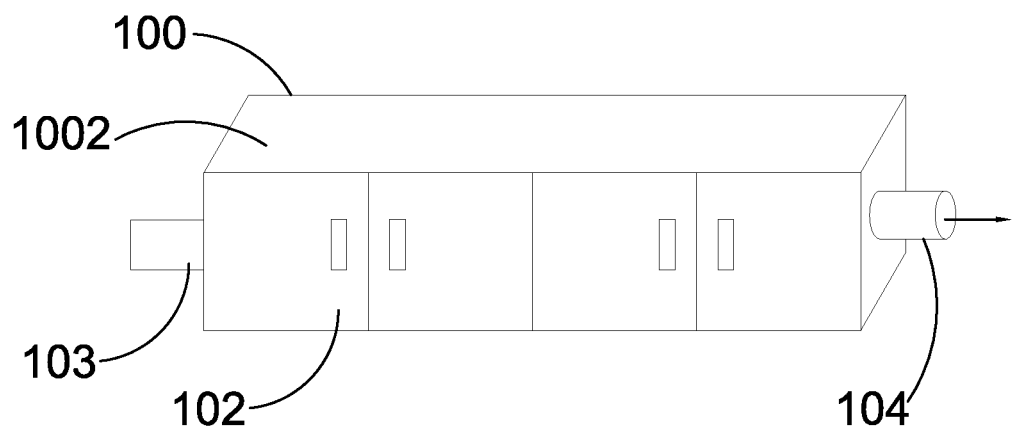
FIG. 6 is an illustration showing the overall appearance of a multifunctional microwave plasma and ultraviolet deodorization treatment unit according to the preferred embodiment of the present invention.

Referring to FIG. 1 of the drawings, a block diagram showing the structure of a multifunctional microwave plasma and ultraviolet deodorization treatment unit is illustrated. The multifunctional microwave plasma and ultraviolet deodorization treatment unit comprises: a rapid decomposition device (1), a high frequency plasma electric field (2), a microwave plasma electric field (3), a high intensity ultraviolet radiation field (4), a low temperature plasma electric field (5), a high intensity ozone gas reaction chamber (6), a reaction termination chamber (7) and a clean gas organization chamber (8) sequentially installed on a wall of and inside a horizontal rectangular box 100, the horizontal rectangular box 100 has a channel cavity inside and along its horizontal axis thereof. An odor collecting pipe for exhaust gas and an odor gas storage cabinet (9) are connected to an air pump (10). The air pump (10) is connected to an odor gas inlet (103) of the rapid decomposition device (1), and a clean gas exhaust pipe (104) is connected at one end of the clean gas organization chamber (8), as shown in FIG. 6 of the drawings.

In particular, organic or foul odor gas subject to deodorization treatment are collected to the odor gas storage cabinet 9 through the odor collecting pipe for exhaust gas and drawn through an air pump to enter into the multifunctional microwave plasma and ultraviolet light deodorization treatment unit of the present invention. Then, the odor gas are guided to flow sequentially to the rapid decomposition device (1), the high frequency plasma electric field (2), the microwave plasma electric field (3), the high intensity ultraviolet radiation field (4), the low temperature plasma electric field (5), the high intensity ozone gas reaction chamber (6), the reaction termination chamber (7) and the clean gas organization chamber (8), thereby the odor gas is treated by multifunctional microwave plasma and ultraviolet light deodorization treatment unit of the present invention to form a discharge gas and the discharge gas is discharged to the natural air. The discharge gas is colorless, odorless and sterilized, which is fresh and safe to the environment.

The rapid decomposition device (1) comprises activated carbon (12) for adsorption function and a monofluoro atom oxide catalyst (14), wherein the monofluoro atom oxide catalyst is commercially available under the trade name sodium monofluorophosphate, and the chemical formula is $Na_2PO_3F$. The activated carbon is arranged to adsorb large particles of gas molecules to filtering gas molecules less than 10,000 mesh. The rapid decomposition device (1) also has an ultraviolet radiation emission arrangement for providing ultraviolet radiation. After ultraviolet radiation, strong decomposition process occurs in the presence of the catalyst and the activated carbon such that the odor gas molecules are reorganized into carbon-, oxygen-, and hydrogenated-containing substances and the odor level is greatly reduced.

The activated carbon plays the role of physical decomposition. The principle is: rapid filtering of gas molecules less than 10,000 mesh and adsorption of large gas particles; after ultraviolet radiation, the catalyst provides a function of chemical decomposition. The principle is: free oxide with monofluoride atom and activated carbon can rapidly adsorb and cleave nitrogen, hydrogen, hydrocarbons, and nitrogen oxynitride organic compounds, and release heat during a strong decomposition process, thus exhibiting chemical bond transfer to acidic substances and alkali substances and losing original characteristics, and the accumulated macromolecules are continuously reorganized into carbon, oxygen, and hydrogenated substances, and the odor is rapidly reduced. The reaction formula is: odor molecules→$CO_X$+CCl+$HCO_X$+$SO_X$+$CF_4$ ... +$OH^-$.

Figure 2:
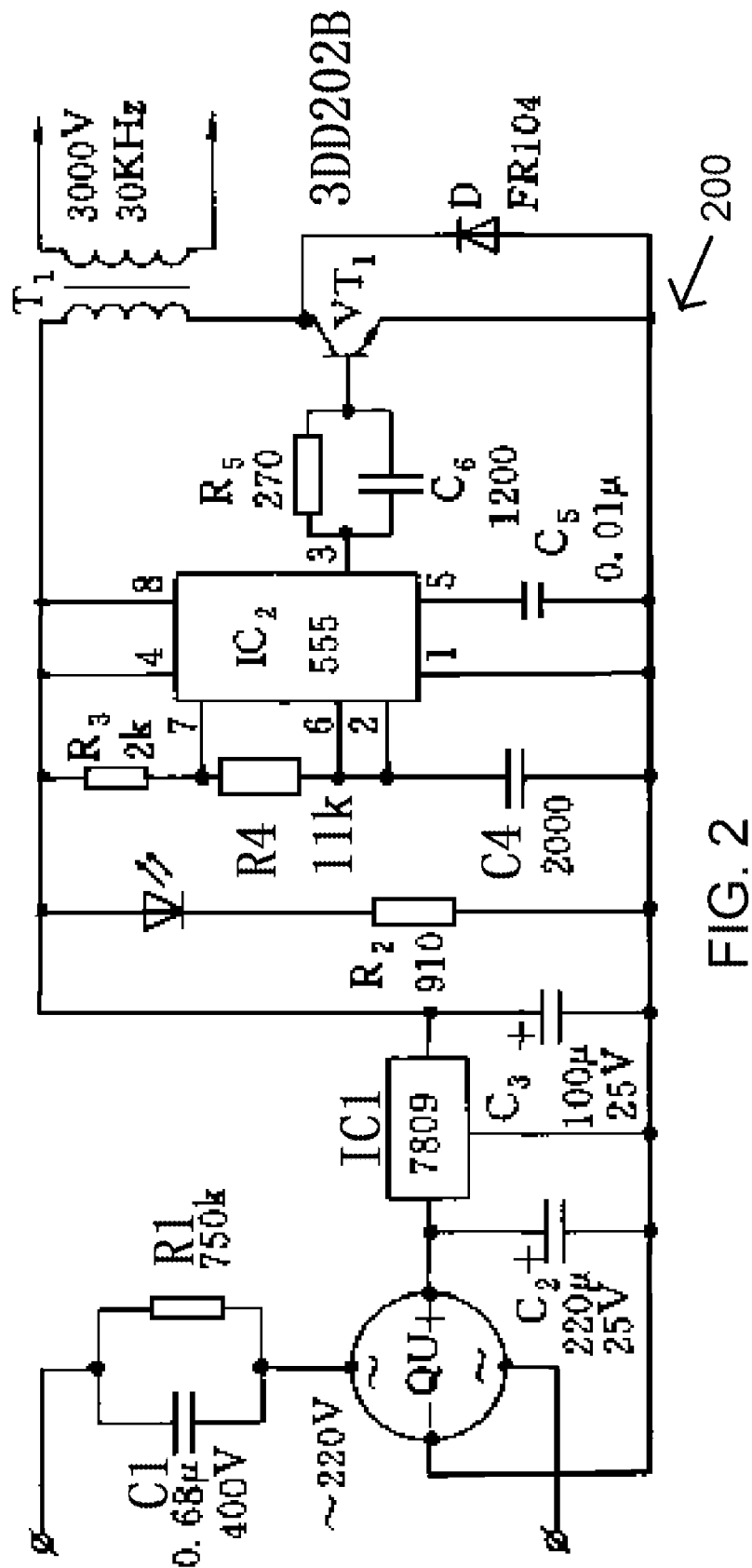
FIG. 2 is a circuit diagram of the high-frequency plasma electric field generator in the high-frequency plasma electric field according to the preferred embodiment of the present invention.

FIG. 2 is a circuit diagram of a high frequency plasma electric field generator (20) in the high frequency plasma electric field (2) of the present invention.

The high frequency plasma electric field (2) comprises a high-frequency plasma electric field generator (20). The high-frequency plasma generated by the high-frequency plasma electric field generator carries out an adaptive oxidation treatment to odor material and the odor material is further oxidized and reduced. When a new oxide is formed from the transformant, this deep treatment creates conditions for structural damage to achieve further deodorization.

In the plasma region, the odor and the bacteria attached to the dust undergo ionization breakdown and chain reaction through the high-frequency plasma electric field, so the dust having a size above 0.5 μm is adsorbed, and reactions to organic matter and bacteria are initiated, the reactions are as follows:

$O_3$ and $OH^-$ react together to produce $O_2^-$ and $HO_2$;
Free radical chain reactions are as follows:
$O_3$ and $O_2^-$ react together to produce $O_3^-$ and $O_2$;
$HO_3^-$ react to produce $O_3^-$ and $H$;
$HO_3^-$ react to produce $OH$ and $O_2$;
$H_2R$ and $OH^-$ react to produce $HR^-$ and $H_2O$;
$3O_3R$, $2OH^-$ and $H^+$ react to produce $2OH^-$ and $4O_2$;
thus permeability distortion of bacteria and virus are produced and the reproduction of molecular organic matters is prevented, and capable of achieving the purpose of disinfection, purification, dust removal and deodorization. By adjusting PR2, the duty cycle of the output square wave can be adjusted by 10%~20%, that is, the microwave output power of the switching power supply module can be adjusted.

Figure 3:
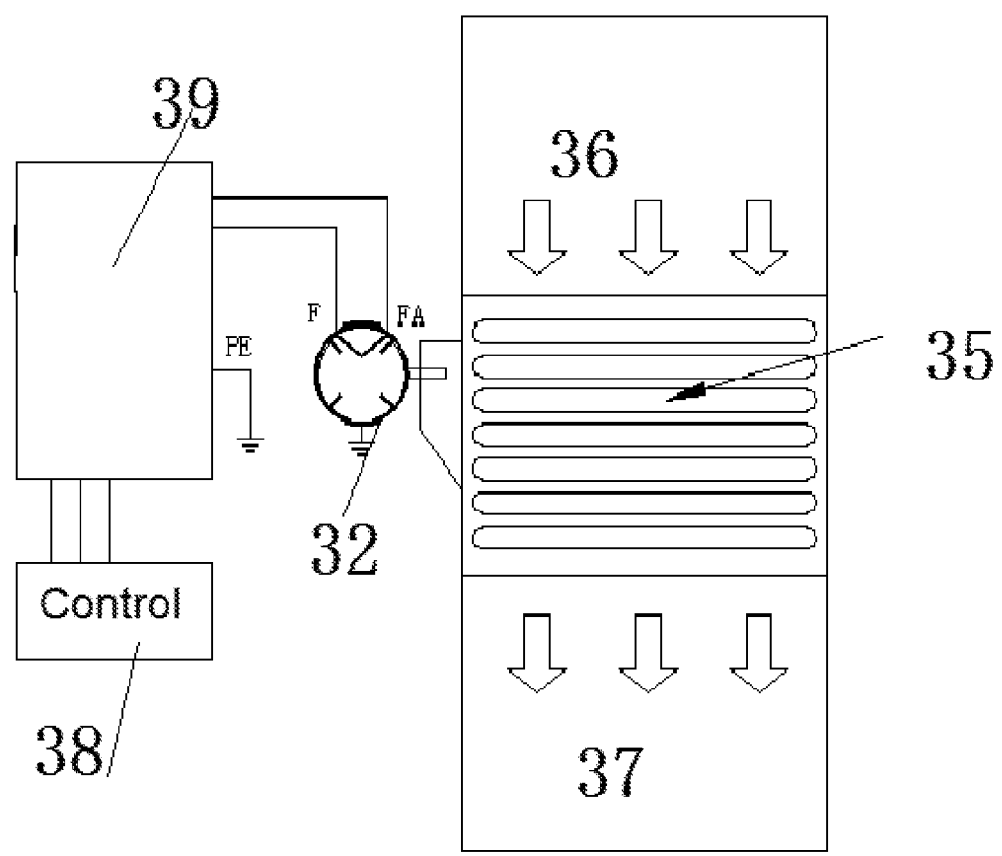
FIG. 3 is a schematic diagram of a microwave plasma electric field (3) according to the preferred embodiment of the present invention.
Figure 5:
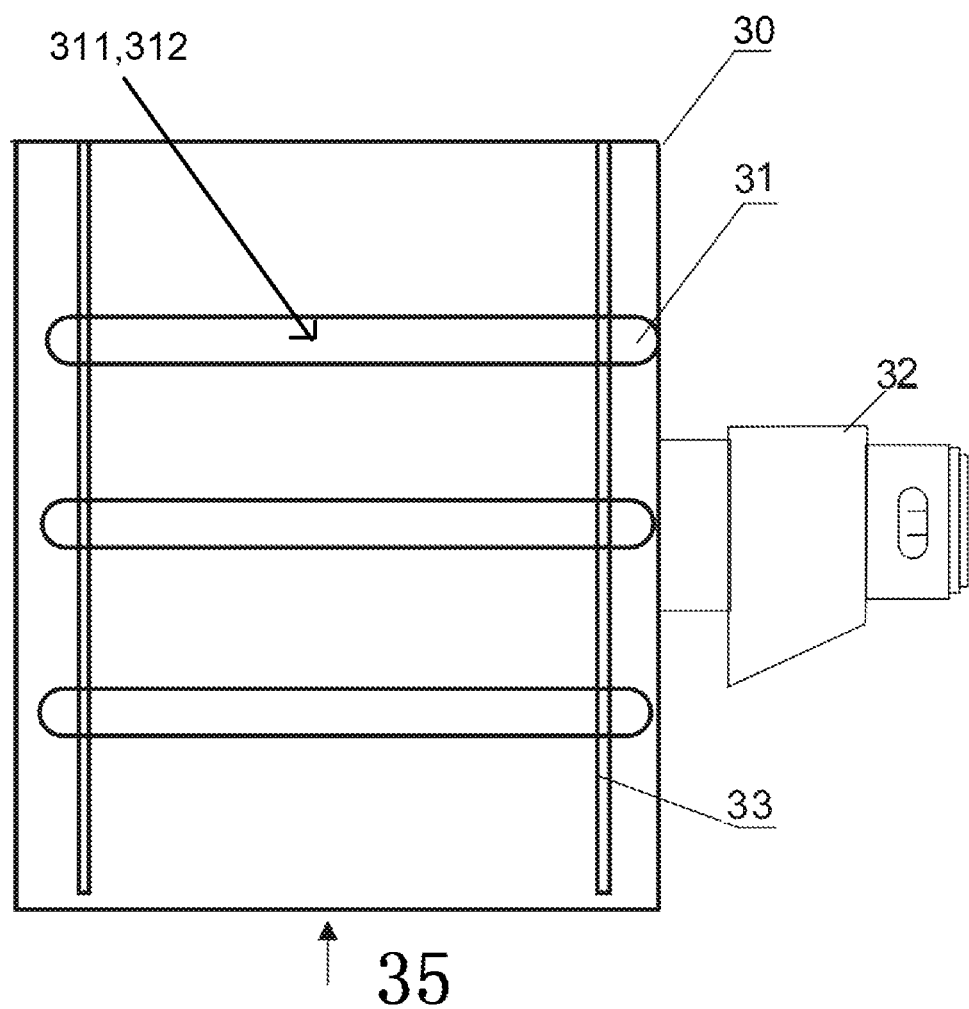
FIG. 5 is a schematic diagram of the mounting structure in the microwave plasma electric field (3) according to the preferred embodiment of the present invention.

FIG. 3 is a schematic diagram of a microwave plasma electric field (3) of the present invention. FIG. 5 is a schematic diagram of the mounting structure in the microwave plasma electric field (3) of the present invention. The numerical references are as follows: quartz tube (31), magnetron (32), bacteria containing odor gas to be treated (36), odor gas outlet after degradation (37), control (38), and high voltage power supply (39). The microwave plasma electric field (3) comprises: a control (38) which is connected to a high voltage power supply (39), the high voltage power supply (39) is connected to the magnetron (32), the microwave plasma electric field (3) has a fixed partition panel (33), and a quartz tube (31) is mounted to the fixed partition panel (33), the magnetron (32) is mounted on the casing (30) of the microwave plasma electric field (3); the quartz tube (31) is filled with an inert gas (311) and mercury (312), and the entire quartz tube (31) is uniformly discharged in the microwave plasma electric field (3), producing a full-band ultraviolet light at 180~380 nm and ozone, and ultraviolet light and ozone are used for sterilization.

Description of triple microwave sterilization technology:
1. Microwave sterilization: When the microwave field acts on a substance, it has thermal effect and non-thermal effect. The non-thermal effect is that the microwave field directly acts on the cell, breaks down the cell wall, breaks the DNA strand, and causes the cell to rupture, thus resulting in death of bacteria or odorous cell modification. 2. Microwave Excitation of UV for deodorization sterilization: ultraviolet light for deodorization sterilization is used. The method of UV deodorization sterilization is as follows: the quartz tube (31) is filled with an inert gas and mercury, and the entire quartz tube is uniformly discharged in the microwave plasma electric field (3), producing a full-band UV at 180~380 nm and ozone, and ultraviolet light and ozone are used for sterilization and the sterilization effect is very obvious. 3. Microwave excitation of ultraviolet light to produce ozone deodorization sterilization: by using quartz tube material, inert gas and mercury ratio, under the action of microwave field, full-band ultraviolet light from 180 nm~380 nm can be generated, the different wavelengths of ultraviolet light will ionize the odor molecules of the odorous gas entering the microwave reaction chamber (35) to produce ozone and then the ozone is used for oxidation, deodorization and sterilization. Compared with the conventional high-pressure discharge method, the ozone produced by the method of the present invention has a high ultraviolet ozone purity and does not produce harmful nitrogen monoxide and nitrogen dioxide. In summary, when the deodorization sterilization technologies of all three elements, microwave, ultraviolet and ozone, work together on odor molecules and bacteria, a deodorization rate of over 98% and the bacterial killing rate of over 99.96% can be achieved. The high-radiation and full-band ultraviolet light generated by the microwave plasma electric field 3 strongly radiates all the gas decomposition of the high-frequency plasma electric field, causing permeability distortion and modification, replication, decolorization, dehydration, cell rupture of the gas molecules, the substances of all of the odor components are here, DNA and RNA are severely damaged, the original activity is lost, and the power of microwave reaches 300 W.

Figure 7:
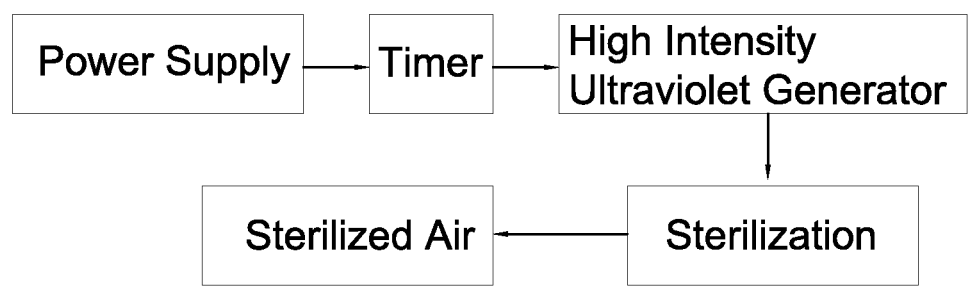
FIG. 7 is a schematic diagram showing the working principle of the high intensity ultraviolet radiation field (4) according to the preferred embodiment of the present invention.
Figure 8:
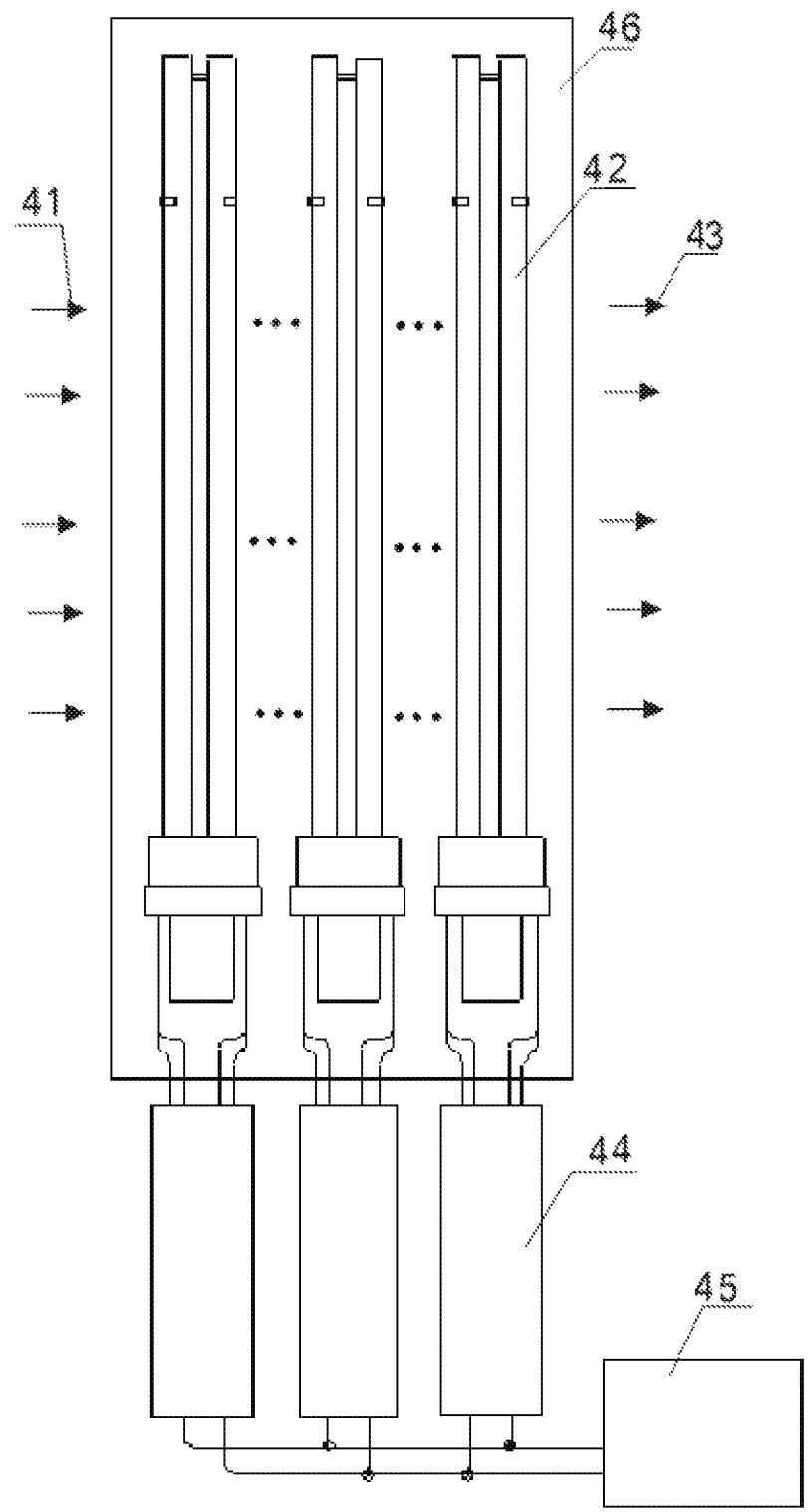
FIG. 8 is a circuit block diagram of the high intensity ultraviolet radiation field (4) according to the preferred embodiment of the present invention.

FIG. 7 and FIG. 8 are schematic diagrams showing the working principle of the high intensity ultraviolet radiation field (4) of the present invention. The high intensity ultraviolet radiation field (4) includes: a controller (45) connected in parallel with a plurality of ballasts (44), each ballast (44) connected to a high intensity ultraviolet generator (42), all of the high intensity ultraviolet generator (42) mounted in a cavity (46) of the high intensity ultraviolet radiation field (4). The high intensity ultraviolet radiation field produces an ultraviolet radiation dose of ≥20000 uw or above, all of the organic odor substances and the bacterial carrying air (41) which pass through the high intensity ultraviolet radiation field are strongly decomposed or replicated into modified molecules, and the residue substances is further cracked into new gas molecules (43), then the gas molecules (43) are discharged.

Figure 9:
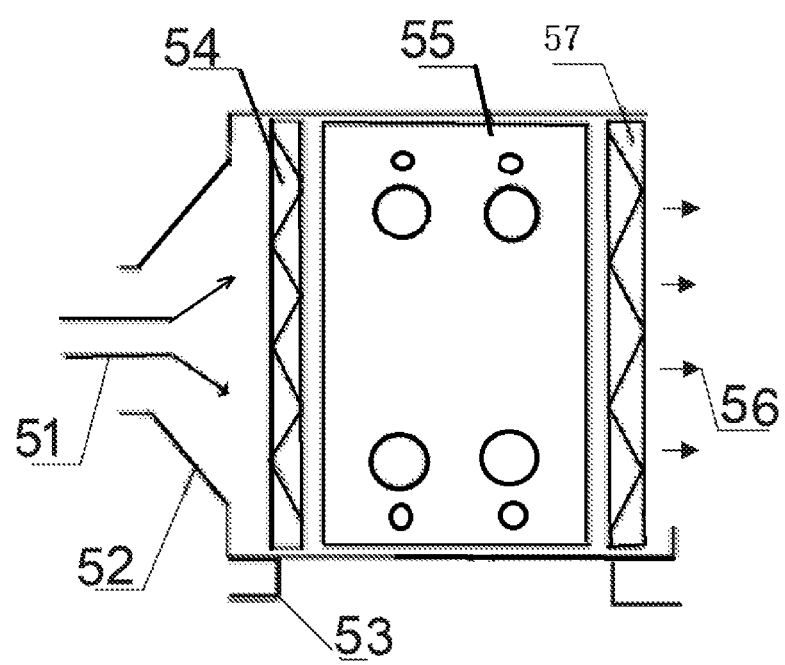
FIG. 9 is a schematic diagram showing the structure of the low temperature plasma electric field (5) according to the preferred embodiment of the present invention.

Referring to FIG. 9 of the drawings, multifunctional microwave plasma and ultraviolet deodorization treatment unit is characterized in that: comprises: inside a casing (52) of the low temperature plasma electric field (5), an inlet air filter (54) mounted proximal to an air inlet (51) of the low temperature plasma electric field (5), an outlet air filter (57) mounted proximal to the air outlet (56) of the low temperature plasma electric field (5), and a low temperature plasma electric field generator (55) mounted in the middle of and inside the casing (52) of the low temperature plasma electric field (5); gas molecules, organic matters and bacteria, after being oscillated at a high frequency in the low temperature plasma electric field, completely lose their life characteristics, then are accelerated by the electric field to generate gas molecules in a plasma state, that further changing the original characteristics and lead to the loss of odor, and transforming into new gas molecules, and its density reaches $2.4 \times 10^{16} \sim 8.9 \times 10^{16}$ m$^3$.

Figure 10:
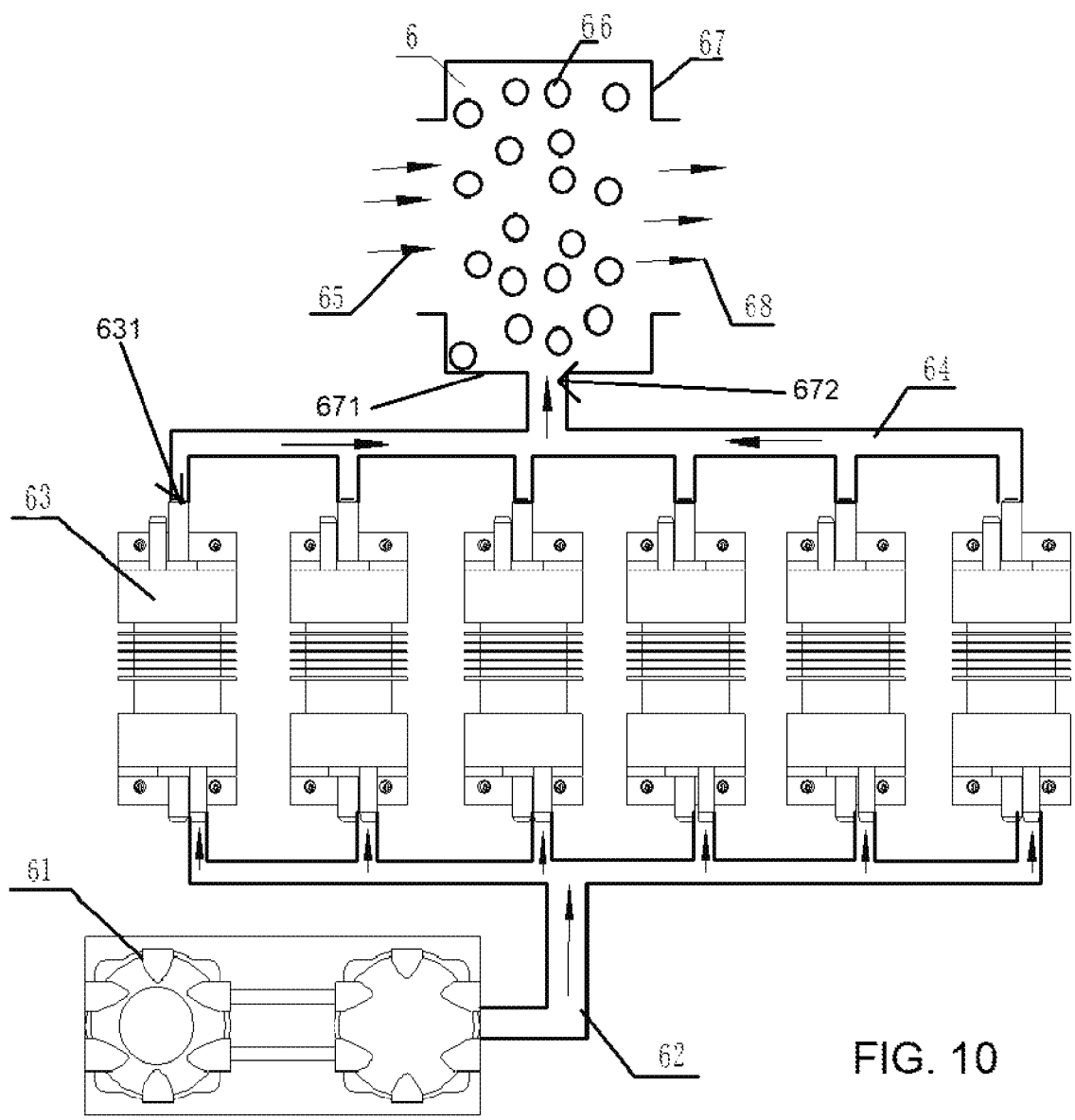
FIG. 10 is a schematic diagram showing the high intensity ozone gas reaction chamber according to the preferred embodiment of the present invention.

Referring to FIG. 10, the high intensity ozone gas reaction chamber (6) comprises: an air compressor (61) connected to an air source gas pipe (62), the air source gas pipe (62) connected in parallel to a plurality of ozone generators (63), and a gas outlet (631) of each of the ozone generators (63) are connected to the ozone gas pipe (64), the ozone gas pipe (64) has one end connected to the ozone gas inlet (672) at the bottom (671) of the high intensity ozone gas reaction cavity (67). All of the gas molecules which are continuously transformed and modified to form low temperature plasma by rapid decomposition, degradation, modification, oxidation, replication, and permeability distortion need to be further oxidized, open-loop, and chain-broken by high intensity ozone gas so that the gas molecules are converted into a clean gas formed in an oxide molecular chain. In FIG. 10, the numerical references are: air compressor (61), air source gas pipe (62), ozone generator (63), ozone gas pipe (64), ozone reaction cavity gas inlet of the high intensity ozone gas reaction cavity (65), ozone gas (66), high intensity ozone gas reaction cavity (67), ozone reaction cavity gas outlet of high-intensity ozone gas reaction cavity (68).

As shown in FIG. 10 of the drawings, the ozone gas (66), which is generated by the ozone generators (63), are collected by the ozone gas pipe (64) and delivered to the high intensity ozone gas reaction cavity (67) through the ozone gas inlet (672). Then, gas molecules flowing from the ozone reaction cavity gas inlet (65) is guided to flow inside the high intensity ozone gas reaction cavity (67) and then exit through the ozone reaction cavity gas outlet (68) to the reaction termination chamber (7).

Figure 11:
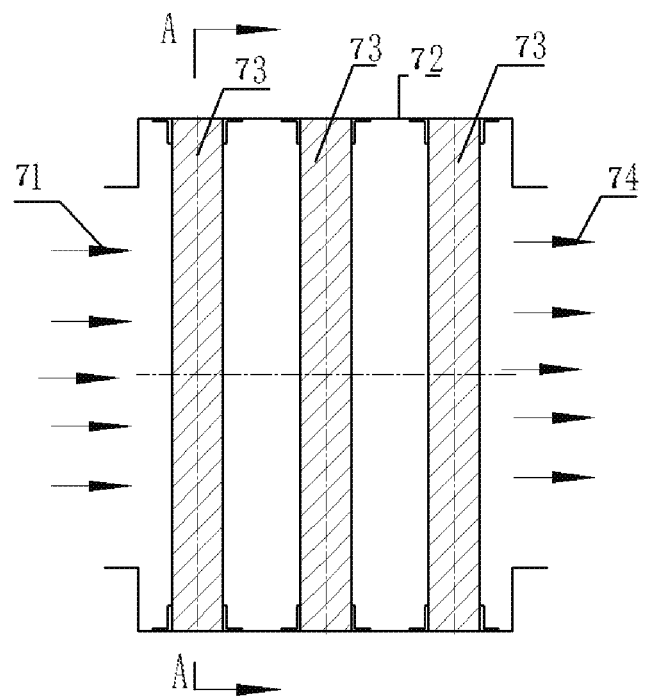
FIG. 11 is a schematic diagram showing the structure of the reaction termination chamber (7) according to the preferred embodiment of the present invention.
Figure 12:
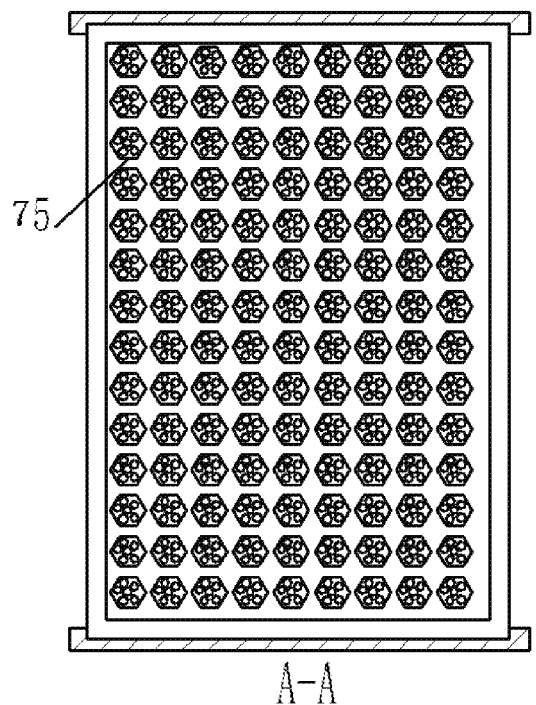
FIG. 12 is a sectional view of the reaction termination chamber (7) in A-A direction according to the preferred embodiment of the present invention.

FIG. 11 and FIG. 12 are schematic diagrams showing the structure of the reaction termination chamber (7) of the present invention. The reaction termination chamber (7) comprises: a plurality of honeycomb activated carbon filters (73) installed in the reaction termination chamber body (72), and the honeycomb activated carbon filter (73) is densely covered with pure carbon (75). In FIG. 11, the numerical references are: inlet of the reaction termination chamber (71), the reaction termination chamber body (72), honeycomb activated carbon filter (73), outlet of the reaction termination chamber (74), and pure carbon (75). After the odorous gas is decomposed, modified, replicated, reduced, and transformed to plasma state, all the reaction processes are terminated here so that no new environmental pollution is caused to the final exhaust gas, all reaction processes are closed by the pure carbon element and composite carbon cavity of 20~10000-A, and the residual odor gas continues to be adsorbed to achieve the purpose of terminating the reaction.

Figure 13:
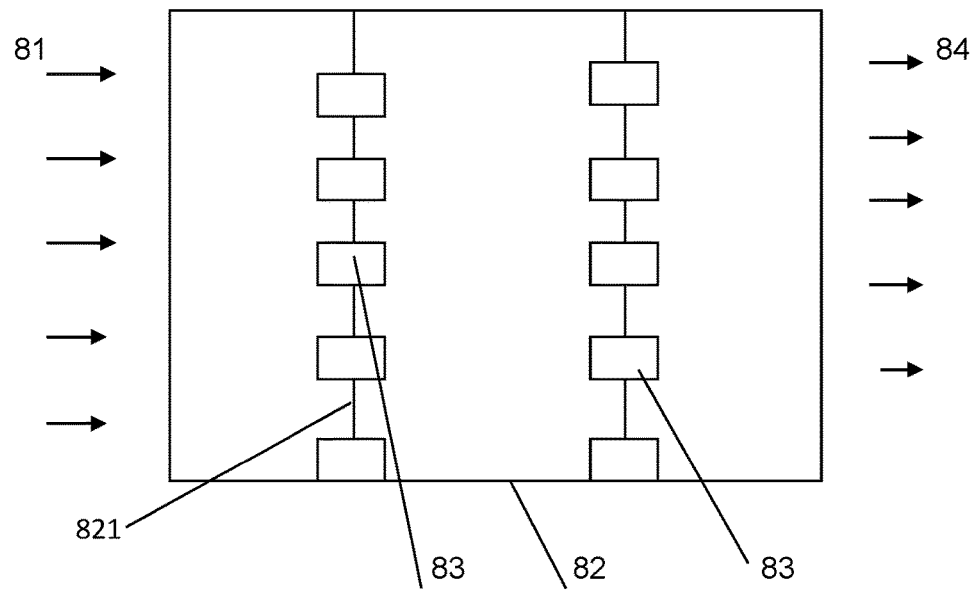
FIG. 13 is a schematic diagram of the clean gas organization chamber (8) according to the preferred embodiment of the present invention.

FIG. 13 is a schematic view showing the installation of the clean gas organization chamber (8) of the present invention. A plurality of positive and negative ion generators (83) are mounted on the frame (821) of the clean gas organization chamber body (82) of the clean gas organization chamber (8). In FIG. 13, the numerical references are: inlet air (81), the clean gas organization chamber body (82), the positive and negative ion generator (83), and the discharged colorless, odorless fresh air (84); the working principle is: the positive and negative ion generator increases the low voltage input through the booster circuit to DC positive high voltage and DC negative high voltage respectively, and the discharge tip is used to generate a high corona from the DC positive high voltage, and the air is ionized to generate a large amount of positive ions. At the same time, another discharge tip is used to generate a high corona from the DC negative high voltage, and the air is ionized to generate a large amount of negative ions. The positive and negative ions, which are generated simultaneously of equal amounts, meet each other in the air for positive and negative charge neutralization, and huge energy release is produced at the moment of neutralization of the positive and negative ions, thereby effectively causing the change of the bacterial structure in the surrounding or the death of bacteria caused by conversion of energy, and hence realizing the bacteria killing function of the positive and negative ion generator. The number of negative ions is greater than the number of positive ions, the excess negative ions floating in the air can effectively purify the dust in the air and improve the quality of oxygen in the air.

FIG. 13 shows the installation structure of the clean gas organization chamber (8). The positive and negative ion generator (83) is an organization device that activates all the gases emitted after the termination of the reaction into oxygen-rich negative oxygen ions for discharge into the outside air. The discharged gas is colorless, odorless and fresh air.

Figure 14:
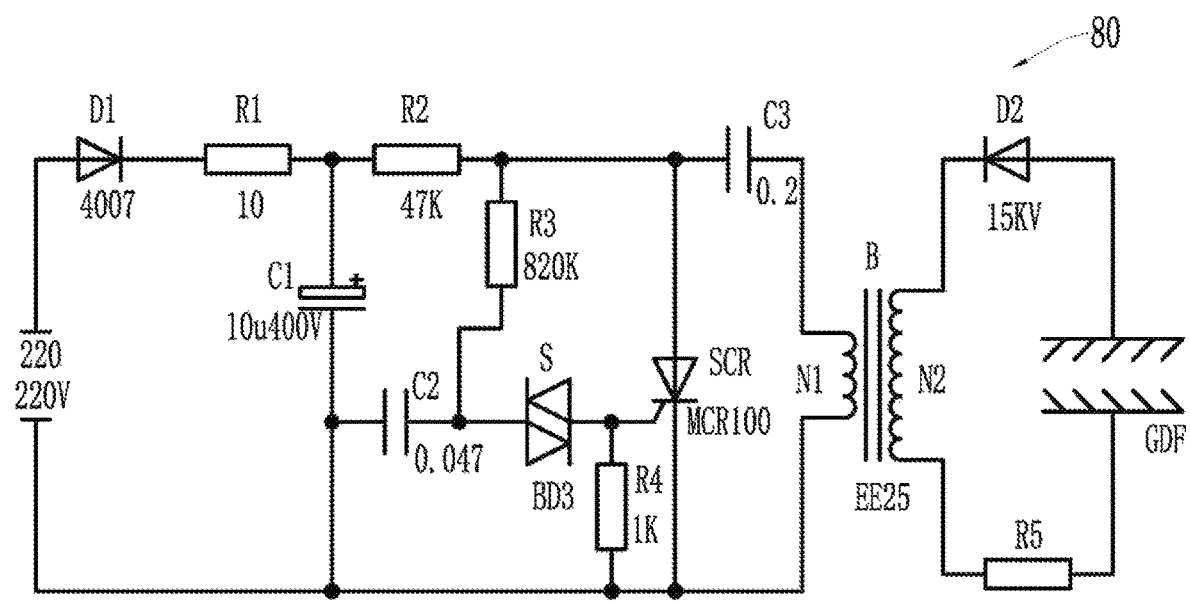
FIG. 14 is a schematic diagram showing the circuit of the clean gas organization chamber (8) according to the preferred embodiment of the present invention.

FIG. 14 is a schematic diagram showing the circuit (80) of the clean gas organization chamber (8) of the present invention, wherein, diode D1, triode SCR model is MCR100, diode D2, transformer B, positive and negative ion generator GDF, resistors R1, R2, R3, R4, R5, Capacitors C1, C2, C3. The rectifier is formed by a diode D1, a resistor R1, and a capacitor C1. The oscillator is formed by a triode SCR and a transformer B. The half-wave rectifier is formed by a diode D2. The rectifier is connected to the oscillator, the oscillator is connected to the half-wave rectifier, and the half-wave rectifier is connected to the positive and negative ion generator GDF. The rectifier rectifies 220V and the oscillator changes the current to a high frequency current. The half-wave rectifier changes the high-frequency current to a DC high voltage. The positive and negative ion generator GDF emits positive and negative ions.

FIG. 6 is an illustration showing the overall appearance of a multifunctional microwave plasma and ultraviolet deodorization treatment unit of the present invention, which is characterized in that: the rapid decomposition device (1), the high frequency plasma electric field (2), the microwave plasma electric field (3), the high intensity ultraviolet radiation field (4), the low temperature plasma electric field (5), the high intensity ozone gas reaction chamber (6), the reaction termination chamber (7) and the clean gas organization chamber (8) are sequentially installed inside a box body (1002) of a horizontal rectangular box (100), the horizontal rectangular box (100) comprises a plurality of doors (102) at a front end thereof for easy installation and maintenance of the equipment inside.

FIG. 2 is a circuit diagram of the high frequency plasma electric field generator in the high frequency plasma electric field (2) of the present invention. The circuit (200) of high frequency plasma electric field generator comprises: a rectifier QU is connected to the voltage regulator IC1 7809, the voltage regulator IC1 7809 is connected to an input terminal of time base circuit of the inverter IC2 555, and an output terminal 3 of the time base circuit of the inverter IC2 555 are connected to a base of an amplifier VT1 through the resistor R5 and capacitor C6, an output of the amplifier is connected to transformer T1 to output high frequency voltage. In FIG. 2, the rectifier QU is connected to the regulator IC1 7809 and outputs a DC voltage, the inverter IC2 555 time base circuit and its peripheral components are used as an oscillator to output high-frequency voltage, which is then amplified by the amplifier VT1 for the transformer T1 to output high-frequency voltage, diode D is model FR104. The model of the amplifier VT1 is 3DD202B.

Figure 4:
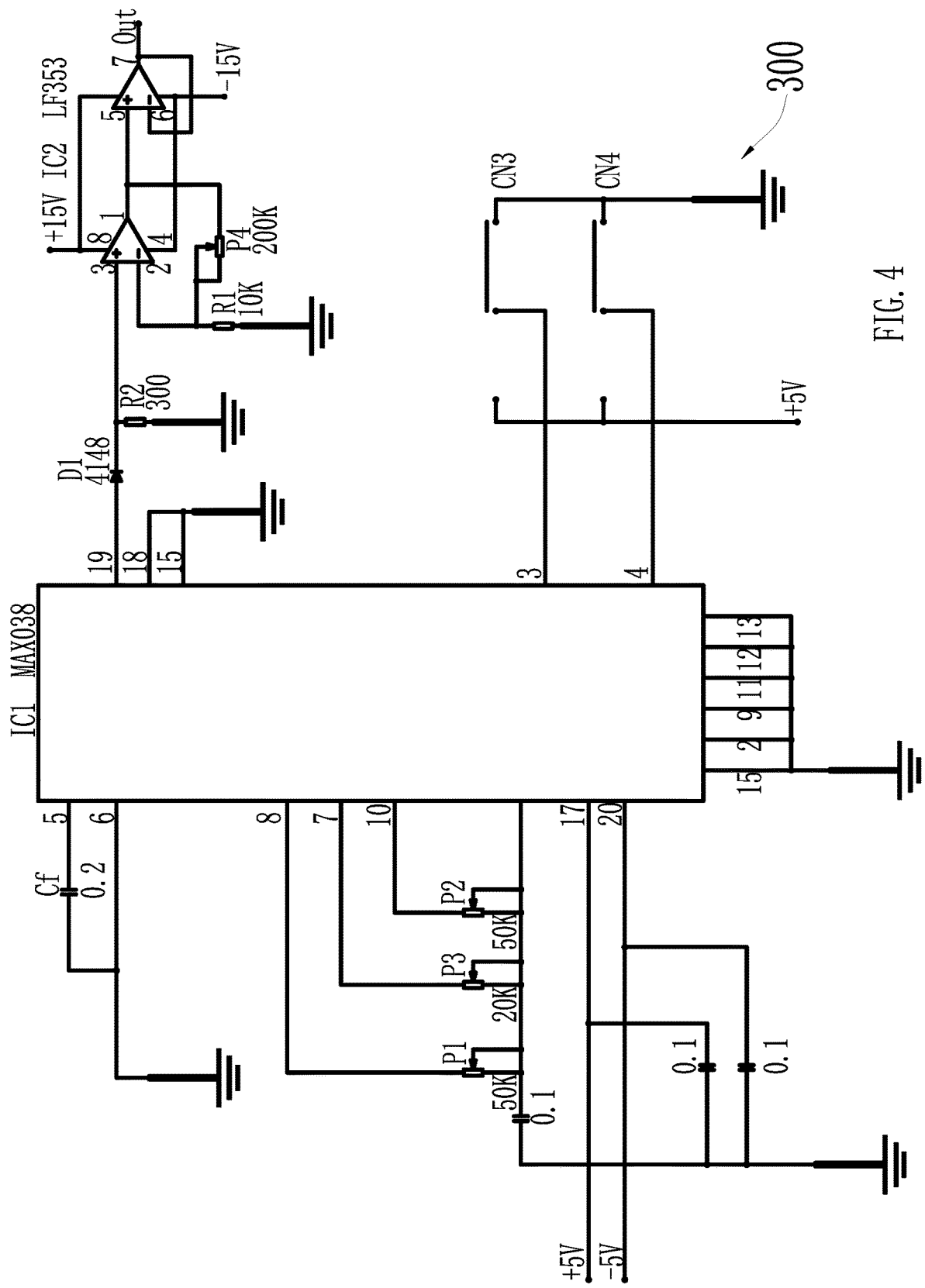
FIG. 4 is a circuit diagram of the high voltage power supply in the microwave plasma electric field (3) according to the preferred embodiment of the present invention.

FIG. 4 is a circuit diagram of the high voltage power supply in the microwave plasma electric field (3). The circuit (300) for providing the high voltage power supply comprises: integrated circuit IC1 MAX038, which is a high frequency precision function signal generator, potentiometer P1 is connected to pin 8 of IC1, potentiometer P3 is connected to pin 7 of IC1, potentiometer P2 is connected to pin 10 of IC1, capacitor C5 is connected to pin 5 of IC1, pin 19 of IC1 is connected to diode D1, D1 is connected to pin 3 of IC2 IF353, pin 17 is connected to +5V power supply, pin 20 is connected to −5V power supply, pin 15, pin 2, pin 9, pin 11, pin 12, pin 13 are grounded, the pin 18 and pin 15 are grounded, pin 3 of IC1 is connected to the CN3 tactile switch, pin 4 of IC1 is connected to the tactile switch CN4, an output of diode D1 4148 is connected to pin 3 of amplifier IC2 LF353. Pin 2 of amplifier IC2 LF353 is connected to resistor R1 and potentiometer P4, pin 1 of amplifier IC2 LF353 is connected to pin 5 of amplifier IC2 LF353. Pin 6 of amplifier IC2 LF353 is connected to pin 7 of amplifier IC2 LF353 output, pin 8 of amplifier IC2 LF353 is connect to the power supply. Working principle: the signal of the control is operated by the potentiometer P1, the potentiometer P2 and the potentiometer P3 respectively to set the output power. The signal is transmitted to the integrated circuit IC1 MAX038, and the integrated circuit IC1 converts the signal of the control into a high frequency signal, then IC1 transmits the signal from pin 19 to IC2 LF353. The IC2 LF353 amplifies the high frequency voltage and outputs it to the magnetron 32. Various waveform curves can be represented by trigonometric equations. A circuit capable of generating a variety of waveforms such as a triangular wave, a sawtooth wave, a rectangular wave (including a square wave), and a sine wave is called a function signal generator. Function signal generators have a wide range of applications in circuit experiments and equipment testing. The function signal generator can be made by general-purpose devices such as transistors and op amp ICs, and more often by a Specialized function signal generator IC. Early function signal generator ICs, such as L8038, BA205, XR2207/2209, etc., have fewer functions, less precision, and the upper frequency limit is only 300 kHz, which cannot generate higher frequency signals, and the adjustment method is not flexible enough. The frequency and duty cycle cannot be adjusted independently, and the two affect each other. In view of this, Maxim has developed a new generation of function signal generator ICMAX038, which overcomes the shortcomings of the above-mentioned chips and can achieve higher technical specifications, which is unmatched by the L8038, BA205, and XR2207/2209 chips. The MAX038 has a high frequency and high accuracy, so it is called a high-frequency precision function signal generator IC.

The above-presented embodiments are preferred examples for implementing the present invention, and the present invention is not limited to the above embodiments. Any non-essential additions and replacements made by those skilled in the art according to the technical features of the technical solutions of the present invention all belong to the protection scope of the present invention.

What is claimed is:

1. A multifunctional microwave plasma and ultraviolet light deodorization treatment unit, comprising: a horizontal rectangular box having an elongated body defining a horizontal axis thereof and a channel cavity inside said elongated body, a decomposition device (1), a high frequency plasma electric field (2), a microwave plasma electric field (3), an ultraviolet radiation field (4), a plasma electric field (5), an ozone gas reaction chamber (6), a reaction termination chamber (7) and a gas organization chamber (8) sequentially installed inside said channel cavity of said horizontal rectangular box, and an air pump; wherein said multifunctional microwave plasma and ultraviolet light deodorization treatment unit is arranged to receive odor gas subject to treatment through an odor gas inlet of said decomposition device (1), and the odor gas is guided by said air pump (10) to flow sequentially through said decomposition device (1), said high frequency plasma electric field (2), said microwave plasma electric field (3), said ultraviolet radiation field (4), said plasma electric field (5), said ozone gas reaction chamber (6), said reaction termination chamber (7) and said gas organization chamber (8), and then the odor gas is discharged from said gas organization chamber (8) through a gas exhaust pipe at one end of said gas organization chamber (8), wherein:

said decomposition device (1) comprises activated carbon for adsorption function and a monofluoro atom oxide catalyst arranged for chemical decomposition after ultraviolet radiation;

said high frequency plasma electric field (2) is generated by a high frequency plasma electric field generator;

said microwave plasma electric field (3) is generated by: a casing, a control, a high voltage power supply (39) connected to said control, a magnetron (32) connected to said high voltage power supply (39) and mounted on said casing of said microwave plasma electric field (3), a fixed partition panel (33) inside said casing of said microwave plasma electric field (3), a quartz tube (31) mounted to said fixed partition panel (33), wherein said quartz tube (31) is filled with an inert gas and mercury such that said quartz tube is uniformly discharged in the microwave plasma electric field (3) along its entire length to produce a full-band ultraviolet light at 180~380 nm and ozone of which the ultraviolet light and ozone are arranged for sterilization; and said ultraviolet radiation field (4) is generated by: a controller (45), a plurality of ballasts (44) connected in parallel with said controller (45), a plurality of high intensity ultraviolet generator (42) mounted inside a cavity (46) of the high intensity ultraviolet radiation field (4) and connected to said plurality of ballasts (44) respectively such that one said high intensity ultraviolet generator (42) is connected to one said ballast (44).

2. The multifunctional microwave plasma and ultraviolet light deodorization treatment unit according to claim 1, wherein said plasma electric field (5) is generated by: a casing (52) having an air inlet (51) and an air outlet (56) at two sides of said casing, an inlet air filter (54) mounted proximal to said air inlet (51), an outlet air filter (57) mounted proximal to said air outlet (56), and a plasma electric field generator (55) mounted inside said casing (52) between said air inlet (51) and said air outlet (56), thereby the odor gas subjected to treatment is guided to flow from said air inlet to pass through said plasma electric field generator so that oscillation in said plasma electric field is achieved;

said ozone gas reaction chamber (6) has an ozone gas reaction cavity and comprises an air compressor (61), an air source gas pipe (62) having one end connected to said compressor and another end connected to a plurality of ozone generators (63) in which said plurality of ozone generators are connected in parallel, an ozone gas pipe (64) having one end connected to said plurality of ozone generators through a gas outlet of each said ozone generator and another end connected through an ozone gas inlet (672) to said ozone gas reaction cavity (67).

3. The multifunctional microwave plasma and ultraviolet light deodorization treatment unit according to claim 2, wherein said reaction termination chamber (7) comprises: a reaction termination chamber body (72), a plurality of honeycomb activated carbon filters (73) installed in said reaction termination chamber body (72), wherein said honeycomb activated carbon filter (73) is covered with pure carbon (75), wherein said gas organization chamber (8) comprises a plurality of positive and negative ion generators (83) mounted on a frame (821) inside said reaction termination chamber body (72), thereby the odor gas is guided to flow from said ozone gas reaction chamber (6) to said reaction termination chamber so that the odor gas is stopped from further reactions after passing through said reaction termination chamber, and then the odor gas is guided to flow from said reaction termination chamber to said gas organization chamber (8) for further sterilization and air purification.

4. The multifunctional microwave plasma and ultraviolet light deodorization treatment unit according to claim 3, wherein said high frequency plasma electric field generator comprises an integrated circuit IC1 with a model number of 7809 and an integrated circuit IC2 time base circuit with a model number of 555.

5. The multifunctional microwave plasma and ultraviolet light deodorization treatment unit according to claim 3, wherein said microwave plasma electric field (3) comprises a voltage power supply in a circuit, which comprises: an integrated circuit IC1 and an integrated circuit IC2.

6. The multifunctional microwave plasma and ultraviolet light deodorization treatment unit according to claim 4, wherein said high frequency plasma electric field generator comprises a rectifier QU connected to a voltage regulator of the integrated circuit IC1 with a model number of 7809, wherein the voltage regulator is connected to an input terminal of an inverter of the integrated circuit IC2 time base circuit with the model number of 555, an output terminal of pin 3 of the inverter of IC2 555 time base circuit passes through resistor R5 and capacitor C6 and connects to a base of an amplifier VT1, an output of the amplifier VT1 is connected to transformer T1 to output high frequency voltage.

7. The multifunctional microwave plasma and ultraviolet light deodorization treatment unit according to claim 5, wherein said integrated circuit IC1 is a high frequency precision function signal generator of which potentiometer P1 is connected to pin 8 of said integrated circuit IC1, potentiometer P3 is connected to pin 7 of said integrated circuit IC1, potentiometer P2 is connected to pin 10 of said integrated circuit IC1, capacitor C5 is connected to pin 5 of said integrated circuit IC1, pin 19 of said integrated circuit IC1 is connected to diode D1, diode D1 is connected to pin 3 of said integrated circuit IC2, pin 17 is connected to +5V power supply, pin 20 is connected to −5V power supply, pin 15, pin 2, pin 9, pin 11, pin 12, pin 13 are grounded, pin 18 and pin 15 are grounded, pin 3 of said integrated circuit IC1 is connected to the CN3 tactile switch, pin 4 of said integrated circuit IC1 is connected to the tactile switch CN4, an output terminal of diode D1 4148 is connected to pin 3 of amplifier of said integrated circuit IC2, pin 2 of amplifier of said integrated circuit IC2 is connected to resistor R1 and potentiometer P4, pin 1 of amplifier of said integrated circuit IC2 is connected to pin 5 of amplifier of said integrated circuit IC2, pin 6 of amplifier of said integrated circuit IC2 is connected to pin 7 of amplifier of output pin of said integrated circuit IC2, pin 8 of amplifier of said integrated circuit IC2 is connect to the power supply.

* * * * *